United States Patent
Harivel et al.

(10) Patent No.: US 10,466,141 B2
(45) Date of Patent: Nov. 5, 2019

(54) METHOD AND DEVICE FOR MEASURING POLLUTANTS CONTAINED IN ENGINE EXHAUST

(71) Applicant: SNECMA, Paris (FR)

(72) Inventors: Nadine Alice Hélène Harivel, Moissy-Cramayel (FR); Jean-Luc Verniau, Moissy-Cramayel (FR)

(73) Assignee: SAFRAN AIRCRAFT ENGINES, Paris (FR)

(*) Notice: Subject to any disclaimer, the term of this patent is extended or adjusted under 35 U.S.C. 154(b) by 335 days.

(21) Appl. No.: 15/029,587

(22) PCT Filed: Oct. 17, 2014

(86) PCT No.: PCT/FR2014/052657
§ 371 (c)(1),
(2) Date: Jun. 29, 2016

(87) PCT Pub. No.: WO2015/055969
PCT Pub. Date: Apr. 23, 2015

(65) Prior Publication Data
US 2016/0305846 A1 Oct. 20, 2016

(30) Foreign Application Priority Data
Oct. 18, 2013 (FR) .................................... 13 60151

(51) Int. Cl.
*G01N 1/22* (2006.01)
*G01M 15/10* (2006.01)
(Continued)

(52) U.S. Cl.
CPC ............ *G01M 15/102* (2013.01); *G01N 1/22* (2013.01); *G01N 1/2247* (2013.01);
(Continued)

(58) Field of Classification Search
CPC ..... G01N 2001/242; G01N 2001/2291; G01N 2001/2092
See application file for complete search history.

(56) References Cited

U.S. PATENT DOCUMENTS 3,885,437 A 5/1975 Reagan
6,357,305 B1 * 3/2002 Witt ..................... G01N 1/2035
73/863.53
(Continued)

FOREIGN PATENT DOCUMENTS

WO WO 2011048294 A1 * 4/2011 ........... G01N 1/2252
WO WO-2014066214 A1 5/2014

OTHER PUBLICATIONS

French Search Report with English Language Translation Cover Sheet, dated Feb. 21, 2014, French Application No. 1360151.
(Continued)

*Primary Examiner* — Jill E Culler
*Assistant Examiner* — Ruben C Parco, Jr.
(74) *Attorney, Agent, or Firm* — Womble Bond Dickinson (US) LLP

(57) ABSTRACT

The invention relates to a method for measuring pollutants contained in an exhaust stream exiting an engine, comprising the steps consisting of: Positioning a probe such that a sampling opening of said probe is positioned on a sampling surface provided at the outlet of the engine in the exhaust stream, and sampling the exhaust stream with said probe; Activating an analysis unit coupled with the probe in order to acquire characteristic data of the exhaust stream sampled by the probe; Controlling a movement of the probe to impart a continuous movement of the sampling opening along a specific trajectory on the sampling surface with constant surface scanning per unit of time, while continuing the sampling and the acquisition of characteristic data of the exhaust stream sampled by the probe; —Processing the data
(Continued)

acquired by the analysis unit to measure the pollutants present in the exhaust stream. The invention also relates to a device for implementing this measuring method.

10 Claims, 2 Drawing Sheets

(51) Int. Cl.
G01N 33/00 (2006.01)
G01N 1/20 (2006.01)
(52) U.S. Cl.
CPC ......... *G01N 1/2252* (2013.01); *G01N 33/004* (2013.01); *G01N 33/0037* (2013.01); *G01N 2001/2092* (2013.01); *G01N 2001/2291* (2013.01); *Y02A 50/245* (2018.01)

(56) References Cited

U.S. PATENT DOCUMENTS

| | | | |
|---|---|---|---|
| 2008/0190168 A1* | 8/2008 | Booker | G01N 1/2202 73/1.25 |
| 2010/0043573 A1 | 2/2010 | Carichon et al. | |
| 2011/0113899 A1 | 5/2011 | Dahler et al. | |

OTHER PUBLICATIONS

International Search Report with English Language Translation, dated Dec. 10, 2014, PCT Application No. PCT/FR2014/052657.

* cited by examiner

METHOD AND DEVICE FOR MEASURING POLLUTANTS CONTAINED IN ENGINE EXHAUST

FIELD OF THE INVENTION

The present invention relates to the measurement of pollutants, and more particularly to the measurement of pollutants present in exhaust pipes at the outlet of engines, for example in exhaust pipes of airplane engines.

STATE OF THE ART

The present environmental background is such that today it is necessary to determine with accuracy the pollutants emitted in any type of field, in particular pollutants emitted by engines.

For example, it is well known that aviation has a quite negative impact with regard to global warming, which tends to worsen gradually as increases air traffic. In order to limit and control these pollution problems, standards have been established requiring accurate determination of the emissions of pollutants notably in order to be able to certify engines before they may be marketed. Thus for example, the International Civil Aviation Organization (ICAO) imposes that engine manufacturers carry out a certain number of tests and of measurements within a highly specific scope in order to determine with accuracy the pollutants emitted by the engines, whether these are the average concentrations of pollutants in the space at the outlet of the engines or further the detailed concentrations of the pollutants ejected by the engine. Thus, the sampling and analysis chain should observe the standard defined by the ICAO so that an engine is certified. Within this scope, the studied pollutants are either gases (CO, $CO_2$, NO and unburnt gases $CH_x$) or solids (fumes, particles).

The constraints for sampling the exhaust stream during the tests are highly significant, and the sampling probe used is immersed in a very hostile medium. The gases actually flow at rates which may attain 300 m/s (mixed streams), with temperatures which may range up to 420 K, the concentration gradients associated with different pollutants may further be very high. Moreover, the engine to be characterized may sometimes be suspended in the test bench at several meters in height, which will further complicate the operation.

Devices have been proposed giving the possibility of measuring certain components of an exhaust stream circulating in a conduit. Document US 2011/0113899 for example proposes a device comprising an exhaust chimney intended to be coupled with the exhaust pipe of an engine, this exhaust chimney integrating a sampling probe mounted so as to be movable in transverse translation and in rotation around its specific axis. Such a device therefore gives the possibility of taking samples to be analyzed in several points of the chimney, but according to limited positions, notably not giving the possibility of probing the whole of the section of the exhaust stream. Further, such a device cannot be used under the limiting conditions of the engine tests mentioned earlier.

A measurement device which has been used for a long time for carrying out pollutant emission tests under such limited conditions consist in a cross-shaped probe. More specifically, this device comprises a circular frame, the dimensions of which are selected for substantially corresponding to the outlet section of the exhaust stream, the sampling probe being formed with four arms or more mounted on the circular frame towards the inside so as to form a cross. Each of these arms comprises several orifices for sampling the exhaust stream often with the shape of needles associated with a suction system. Such a measurement device thus gives the possibility of sampling the exhaust stream immediately at the outlet of the engine in several points at the same time at the selected sampling surface. This device is however not suitable for taking measurements of the exhaust stream in any point of the sampling plane. Thus, before the measurement steps as such, it is necessary to carry out mapping in order to globally analyze the outlet section of the exhaust stream and thus determine the possible inhomogeneous areas which would distort the measurements carried out in a reduced number of sampling points. This mapping therefore allows selection of the positioning of the cross-shaped probe with respect to the outlet section of the exhaust stream. In order to facilitate this positioning, the ring bearing the arms forming the probe may generally be rotated by means of an indexable system.

Such a measurement device however comprises a certain number of drawbacks which should be solved today in order to be able to conduct more reliable measurements, more rapidly and more easily. In particular, the time for conducting measurements of pollutants with such a cross-shaped probe is very long, which is notably due to the fact that it is absolutely necessary to establish prior to each measurement, detailed mapping of the outlet section of the exhaust stream, which strongly depends on the studied engine, and which should accordingly be established again for each new engine. Such a cross-shaped probe further has the major drawback of requiring a design and dimensioning highly specific to the studied engine, and more specifically to the outlet section of the exhaust stream of said engine. It is thus necessary to manufacture a new device, frame and cross-shaped probe, for each new tested engine, which is economically not very viable, and which is further time consuming. Further, such a device has great bulkiness which makes its handling difficult. Finally, as specified above, it only allows a measurement of pollutants, within a reasonable time only on a limited number of sampling points of the sampling surface, making the measurements of pollutants less reliable.

Document U.S. Pat. No. 3,885,437 describes a device for measuring pollutants which allows sampling on an extended section of the gas stream to be analyzed. In particular, the proposed device is laid out inside a conduit in which flows the gas to be analyzed, and consists in a sampling probe translationally mounted on an arms which may itself rotate around the longitudinal axis of the conduit. The sampling probe describes an Archimedes' spiral movement during the gas sampling. Such a device however does not meet the test constraints mentioned earlier. In particular, this device does not allow analysis of the gases at the immediate outlet of the engine, since it has to be installed inside a conduit. Further, it has an operation and a configuration not allowing it to be adaptable to any types of conduits and/or engines. Finally, even if it allows gas sampling over an extended surface of the section of the gas stream, the analysis of the sampled data remains long and complex to apply.

An object of the present invention is therefore to propose a method and a device for measuring pollutants contained in the exhaust pipe at the outlet of an engine which gives the possibility of solving at least one of the aforementioned drawbacks.

More specifically, an object of the present invention is to propose a method and a device for measuring pollutants contained in the exhaust at the outlet of an engine giving the possibility of carrying out reliable measurements of pollutants, highly representative of the studied exhaust stream, and this in a reduced global time as compared with existing methods and devices.

An object of the present invention is further to propose a method and a device for measuring pollutants contained in the exhaust at the outlet of an engine which does not require preliminary mapping of the outlet section of the exhaust stream.

DISCUSSION OF THE INVENTION

For this purpose, a method for measuring the pollutants contained in an exhaust stream exiting an engine is proposed, comprising the following steps:
  positioning a probe so that a sampling orifice of said probe is placed on a sampling surface provided at the outlet of the engine in the exhaust stream, and sampling the exhaust stream with said probe;
  activating an analysis unit coupled with the probe in order to carry out acquisition of characteristic data of the exhaust stream sampled by the probe;
  controlling a displacement of the probe in order to impart a continuous displacement of the sampling orifice according to a trajectory specific to the sampling surface, while continuing the sampling and acquisition of characteristic data of the exhaust stream sampled by the probe;
  processing the data acquired by the analysis unit in order to measure the pollutants present in the exhaust stream.

Preferably, the displacement of the probe is controlled so that its trajectory corresponds to surface sweeping per constant unit of time.

Preferred but non-limiting aspects of this method, taken alone or as a combination, are the following:
  the displacement of the probe is controlled for imparting a continuous displacement of the sampling orifice according to a specific trajectory in circles, said specific trajectory in circles being formed with several concentric circles of various radii and of at least one segment connecting each adjacent circle, the circles being covered one after the other inwards or outwards with respect to the center.
  the specific trajectory in circles is defined by dividing the sampling surface into a plurality of concentric crowns all having an identical area, each circle of the specific trajectory in circles corresponding to the circle of the middle of each crown.
  the displacement velocity of the sampling orifice of the probe is adapted for each circle of the specific trajectory in circles, so that each circle is covered during the same period.
  the characteristic data of the exhaust stream sampled by the probe are acquired at the same frequency during the whole measurement.
  the data acquired by the analysis unit are processed for determining the nature and the concentration of gases contained in the sampled exhaust stream.
  the data acquired by the analysis unit are processed for determining the nature and the amount of fumes contained in the sampled exhaust stream.
  a filter is used for acquiring the characteristic data of fumes contained in the sampled exhaust stream, the filter then being studied for measuring the fumes present in the exhaust stream on the whole of the sampling surface.
  the data acquired by the analysis unit are processed in correlation with the position of the sampling orifice of the probe.
  the method comprises a preliminary step for activating the probe in order to begin with sampling gas at the sampling orifice towards the analysis unit.

According to another aspect, a measuring device is proposed giving the possibility of applying the method above.

More specifically, a device for measuring pollutants contained in an exhaust stream at the outlet of an engine is proposed, characterized in that it comprises:
  a single probe having a single orifice for sampling the exhaust stream;
  a robot comprising a jointed arm on which is mounted said probe, the robot further comprising means for positioning the sampling orifice of the probe in different points of a sampling surface at the outlet of the engine;
  an analysis unit provided for carrying out continuous acquisition of characteristic data of the exhaust stream sampled by the probe;
  a control unit of the robot provided for imparting a continuous displacement of the sampling orifice of the probe along a specific trajectory over the sampling surface;
  a processing unit provided for processing the data acquired by the analysis unit for measuring the pollutants present in the exhaust stream.

Preferably, the control unit is provided for imparting displacement to the probe with a trajectory corresponding to surface sweeping per constant unit time.

Preferred but non-limiting aspects of this device, taken alone or as a combination, are the following:
  the analysis unit comprises an absorption analyzer which does not scatter radiation for analysis of CO or $CO_2$, and/or a hydrocarbon analyzer with flame ionization, and/or a chemoluminescence analyzer for analysis of NO or $NO_x$.
  the analysis unit comprises at least one filter for capturing fumes present in the exhaust stream.

DESCRIPTION OF FIGURES

Other features and advantages of the invention will further become apparent from the description which follows, which is purely illustrative and non-limiting and should be read with reference to the appended drawings, wherein.

DETAILED DESCRIPTION OF THE INVENTION

Figure 1:
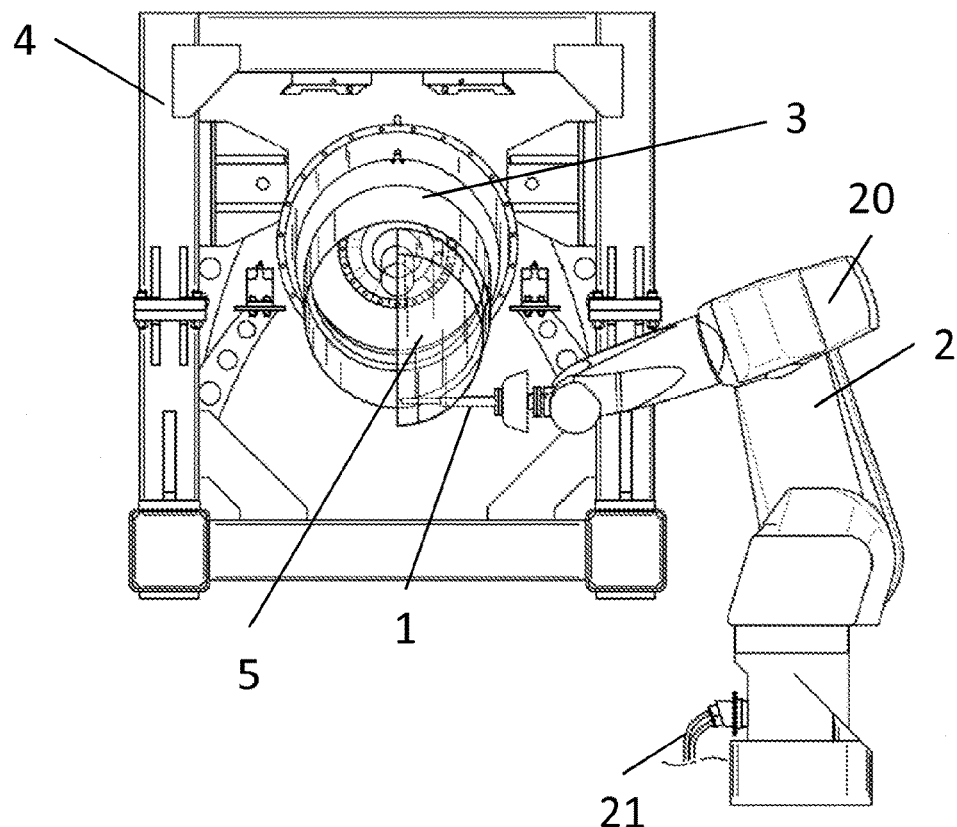
FIG. 1 illustrates a device for measuring pollutants according to the invention placed at the outlet of an engine.

As illustrated in FIG. 1, the use of a device for measuring pollutants is proposed, having as main characteristic the fact of having a movable probe 1 comprising a single orifice 10 for sampling the exhaust stream.

This probe 1, which may also be called a sampling probe, is mounted on the jointed arm 20 of a robot 2. The robot 2 comprising the probe 1 is intended to be positioned at the outlet of an engine 3, for which it is sought to measure the pollutants emitted in the exhaust stream. As illustrated in FIG. 1, the engine 3 may be maintained on a frame 4 or be suspended, the probe 1 borne by the robot 2 then being positioned in the continuity of the engine 3.

The robot 2 with its jointed arm 20 are provided for allowing the probe 1 to be moved in different points at the outlet of the engine 3. More specifically, the robot 2 comprises means for positioning the sampling orifice 10 of the probe 1 in different points of a sampling surface 5 at the outlet of the engine.

The sampling surface 5 is defined beforehand and corresponds to the surface representative of the area where the pollutants are to be measured. This sampling surface 5 has a shape which generally depends on the outlet section of the exhaust gas from the engine 3. The sampling surface 5 is preferably planar, in which case this is referred to as a sampling plane.

When the outlet section of the exhaust is circular, for example it is possible to use a planar sampling surface 5 having the shape of a disc.

Preferably, the robot 2 is such that it allows positioning of the sampling orifice 10 of the probe 1 in any points of the sampling surface defined at the outlet of the engine.

Figure 2:
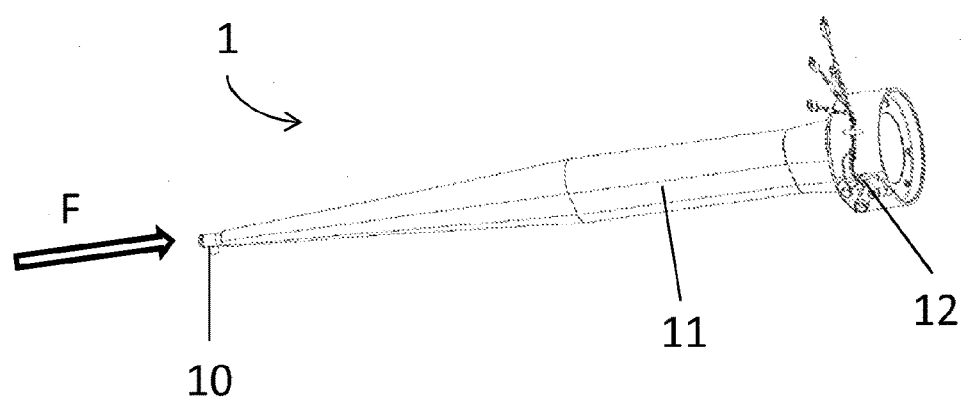
FIG. 2 illustrates a sampling probe used in the device of FIG. 1.

According to an embodiment illustrated in FIG. 2, the single-orifice probe 1 used comprises a sampling orifice 10 appearing as a conical needle.

The probe may further comprise a tubular body 11 through which the sampled exhaust stream circulates from the inlet of the probe at the sampling orifice until it is analyzed.

Preferably, the probe 1 also comprises a rigid casing which will surround the transport tubular body 11. This rigid casing in particular allows protection of the tube for conveying the hot gases and stiffening the probe 1 as such.

According to a specific exemplary embodiment, the probe 1 is in steel and it has a sampling orifice 10 having an aperture with a diameter of 3 mm. The probe 1 may for example have a global length of the order of 70 cm.

Conventionally, the probe 1 comprises a suction system giving the possibility of circulating the sampled gases at the sampling orifice in a set of conduit(s) as far as an analysis unit provided for analyzing the gases sampled by the probe.

The shown measurement device then also comprises an analysis unit which is provided for carrying out continuous acquisition of characteristic data of the exhaust stream sampled by the probe 1.

Such an analysis unit may comprise several types of analyzer(s) depending on the type and on the nature of the pollutant which one seeks to measure. The acquisition of characteristic data of the exhaust stream may be accomplished by the analyzer itself or by a specific acquisition device which gives the possibility of recording the data received by the analyzer.

When it is sought to measure gas pollutants, the analyzers are actually generally coupled with a device giving the possibility of recording the analysis data.

The analysis unit may for example be a non-dispersive absorption analyzer of infrared radiation for analysis of CO or $CO_2$, and/or a hydrocarbon analyzer by flame ionization, and/or a chemoluminescence analyzer for analysis of NO and $NO_x$. According to these examples, a computer system is generally also provided for recording the analysis data from the analyzers.

In other cases, the analyzer used in the analysis unit itself gives the possibility of recording the characteristic data of the exhaust stream. For example, when it is desired to measure solid pollutants, such as fumes or particles, an analyzer may be used appearing as a filter, this filter accumulating the characteristic data of the solids contained in the exhaust stream, carrying out at the same time a continuous acquisition of these characteristic data.

According to a particular embodiment, one or several analyzers are laid out at the probe, for example at the outlet of the sampling probe 1 as illustrated in FIG. 2.

Moreover, a control unit 21 of the robot 2 is provided, which allows actuation of the movement of the jointed arm 20 of said robot 2, and thus movement of the probe 1 preferably attached to the end of the jointed arm 20.

This control unit 21 is provided for imparting a continuous displacement of the sampling orifice 10 of the probe 1 along a trajectory specific to the sampling surface. This displacement trajectory is specifically defined according to the desired measurements, as this is explained later on in the text.

Finally, a processing unit is provided for processing the data acquired by the analysis unit in order to measure the pollutants present in the exhaust stream. This processing unit not only allows determination of the nature of the pollutants present in the exhaust stream but also specific characterization, notably in terms of concentration and of spatial distribution following the sampling surface.

In the case of gas analyzers, the processing unit may for example directly process the acquired/recorded data for inferring therefrom the characteristics of the gas pollutants in the whole of the exhaust stream at the outlet of the engine.

For analysis of solids, of the fumes or particles type, where an analyzer is used as a filter, the processing unit may for example comprise a reflectometer giving the possibility of measuring the reflectivity of the accumulated fume particles on the filters. This device gives the possibility of specifically characterizing the fumes from the exhaust stream, notably in terms of "a smoke number" and of spatial distribution following the sampling surface.

The measurement device as such, and notably the association of a single-orifice probe 1 with a robot 2, has a certain number of advantages as compared with the known devices.

First of all, the manufacturing of the single-orifice probe is much simpler than a multi-orifice cross-shaped probe. Thus, it consists of a single tube for transporting the sampled exhaust stream, it does not include any connections between the tubes. Moreover, it is easier to thermally isolate than a multi-orifice cross-shaped probe since it only includes a single transport tube, having a simple shape. Finally, such a single-orifice probe perturbs less the jet when it is smaller.

The association of the probe with the robot gives the possibility of having a measurement device adapted to engines of different sizes since the robot allows easy displacement of the probe to the different selected sampling points.

Further, the sampling probe may be very rapidly retracted into a retracted position, within a few seconds, for example for positioning it out of the exhaust stream if a risk of burning is detected, which guarantees better safety.

Further, the robot is much easier to use than a measurement device of the type with a rotating ring. The robot is actually totally adaptable and flexible since the control unit comprises a piece of software giving the possibility of selecting any trajectory for the probe. Further, all the areas of the sampling surface may be finally explored, which gives the possibility of having more representative pollutant measurements of the reality.

Moreover, as this will be seen later on, as all the sampling surface may be easily covered, the corresponding analyses in terms of pollutants are more representative of the global sampling surface which gives the possibility of avoiding a preliminary step for mapping the sampling surface only required by the need for selecting the sampling points. This is true regardless of the nature of the measured pollutants, as gases, fumes, or even particles.

The preferred operation of such a measurement device consists of positioning the sampling probe 1 in the exhaust stream F, preferably in a way substantially parallel to said stream F (see FIG. 2), and of continuously analyzing the characteristic data of the exhaust stream sampled by the probe 1.

While analyzing the stream sampled by the probe 1, this same probe 1 is moved in the exhaust stream so as to be able to acquire the characteristic data of the stream in different points of the sampling surface.

The continuous displacement of the probe 1 and the continuous acquisition of characteristic data of the exhaust stream sampled by this probe 1 have the advantage of allowing a detailed analysis of the pollutants present in a given point of the sampling surface continuously, i.e. without having to wait for a dead time during which no analysis is possible, this dead time corresponding to the duration required for the stream to attain the analyzer from the sampling orifice. Indeed, with the proposed measurement method, the stream to be analyzed continuously arrives at the analysis unit and the acquisitions of data are successive, time-shifted without any dead time between each significant acquisition.

According to a particular embodiment, the method proposed for the measurement of pollutants contained in an exhaust stream at the outlet of an engine, therefore comprises a step consisting of positioning the probe 1 so that the corresponding sampling orifice 10 is placed on the sampling surface provided at the outlet of the engine in the exhaust stream. As specified above, this sampling surface may be planar, for example a disc-shaped sampling plane.

Before or after having positioned the probe 1, it should be activated in order to begin the sampling. To do this, for example it is possible to start the suction device if necessary, which gives the possibility of circulating the gases from the sampling orifice of the probe through the associated circulation conduits.

According to a preferred embodiment, the probe is activated before positioning it in the exhaust stream, which gives the possibility of having faster reactivity for measurements. The fact of sucking up the gases before putting the probe in the exhaust stream gives the possibility of avoiding plugging of the probe with fume particles which would accumulate if the probe was placed in the exhaust stream without activation of the suction.

Further, the analysis unit should be activated in parallel for beginning acquisition of characteristic data of the exhaust stream sampled by the probe. It should be noted that the activation of the acquisition is preferably made before activation and initial positioning of the probe, the non-significant data of the exhaust stream in this case being suppressed or not processed.

The acquisitions which are made during activation of the probe become significant of the exhaust stream at the positioning point of the sampling orifice 11 on the sampling surface after having waited for a period at least equal to the dead time required so that the stream attains the analyzer.

After having exceeded this dead time, it is possible to control the displacement of the probe 1 in order to impart a continuous displacement of the sampling orifice 11 along a trajectory specific to the sampling surface, while continuing the sampling and the acquisition of characteristic data of the exhaust stream sampled by the probe 1. Each acquisition is thus directly utilizable, after removing data acquired during the initial period corresponding to the dead time, since the exhaust stream arrives, shifted in time, this shift may be correlated with the displacement velocity of the probe and with its trajectory in order to determine to which position this corresponds on the sampling surface.

Once all the characteristic data of the stream are acquired, they may be processed for measuring the pollutants present in the exhaust stream, and characterizing them at best, in a way correlated with the positioning of the samplings at the sampling surface.

The proposed measurement method gives the possibility of gaining a significant time as compared with measurements carried out discretely since all the dead times are quasi-suppressed, except for the dead time corresponding to the data acquisition at the first point.

The suppression of the data acquired during the dead time by the analysis unit, notably with the gas analyzers, is generally made by the processing unit, in post-processing.

When solid pollutants are measured, such as for example when a filter is used for measuring the fumes, the filter is placed in the circulation conduits of the exhaust stream in a shifted time, i.e. after having waited for a duration at least equal to the dead time.

According to the proposed measurement method, a specific trajectory is selected on which are desirably acquired the characteristic data of the stream.

If a preliminary mapping of the outlet section of the exhaust stream has been carried out in order to determine the representative areas of the exhaust for the measurements of pollutants, this specific trajectory may be based on said mapping. The fact of having a displacement and a continuous acquisition of characteristic data of the sampled exhaust stream will give the possibility of having measurements just as significant, or even more detailed than with a measurement with a multi-orifice probe.

However it is not necessary to be limited to the representative areas defined during the mapping of the outlet section of the exhaust stream, and it is actually possible to opt for a trajectory giving the possibility of covering the largest portion of the sampling surface, which avoids making a selection of sampling areas with respect to the sampling surface.

Figure 3:
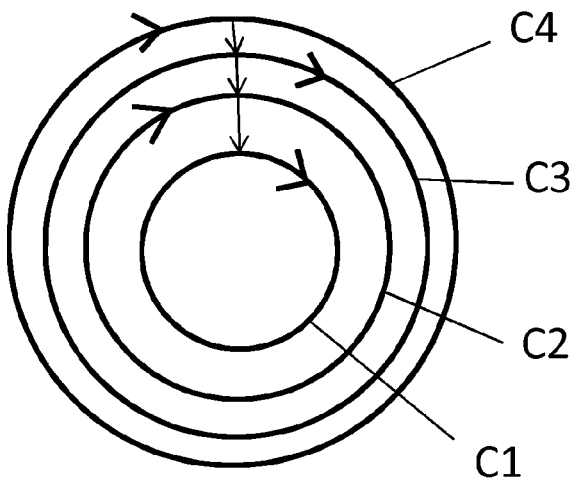
FIG. 3 illustrates the trajectory in circles which may be covered by the sampling probe for conducting measurements of pollutants.

Preferably, a displacement of the probe along a trajectory in circles as illustrated in FIG. 3 is used. Such a trajectory in circles is for example formed with several concentric circles of various radii and with one or several segments connecting two adjacent circles. The trajectory in circles illustrated in FIG. 3 comprises four concentric circles C1, C2, C3, C4, or two adjacent circles are connected by a single segment.

The probe is then moved so that the sampling orifice covers each circle one after the other, which allows the probe to cover an extended sampling surface, delimited by the surface of the circle with the largest radius.

Still preferably, the various circles are covered one after the other inwards or outwards with respect to their common center.

The specific trajectory in circles may be defined in different ways, notably depending on the processing of the acquired data which is desirably carried out subsequently.

For example when the pollution level is obtained by averaging the data taken in the sampling plane, it is important to have the same surface sweeping per unit time.

Figure 4:
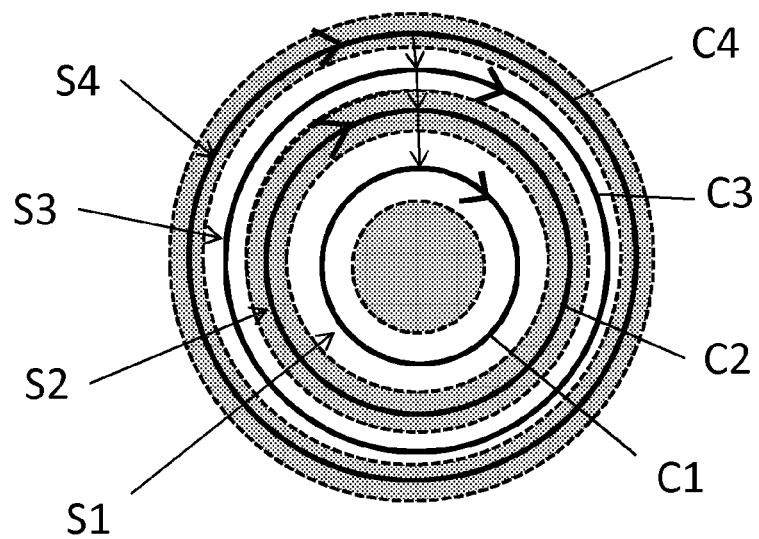
FIG. 4 illustrates the rings with an iso-section giving the possibility of determining the trajectory in circles to be performed by the sampling probe.

In this respect, the measurements of pollutants are preferably carried out with an iso-section. The samplings of the exhaust stream are in this case sucked up at the center of the crowns of same section (S1=S2=S3=S4) in order to have the same surface section per crown, as this is illustrated in FIG. 4.

In order to thereby define a trajectory in a circle with an iso-section, the sampling surface is divided into a plurality of concentric crowns all having an identical area, and each circle of the specific trajectory in circles therefore corresponds to the circle positioned in the middle of each crown.

The exhaust stream is sampled continuously and the acquisitions are made regularly also continuously, according to the frequency imposed by the analysis unit.

In order to observe the criterion of surface iso-sweeping, each circle is preferably swept during the same period but at different velocities. The displacement velocity of the sampling orifice of the probe is therefore in this case a maximum on the outer circle.

The samplings and acquisitions according to this method allow rapid exploration of the whole of the sampling plane. The concentration of the outlet plane is for example obtained by averaging all the data acquired after having suppressed the acquisitions corresponding to the initially present gases in the pipes (a dead time corresponding to the transport duration in the pipes as far as the analysis unit).

The data acquired by the analysis unit are processed so as to determine the nature and the concentration of gases contained in the sampled exhaust stream. This processing may be carried out with any type of known method and available to one skilled in the art.

For the measurement of gas pollutants, various types of analyzers may be used. For example, it is possible to use analyzers of the infrared radiation non-dispersive absorption type for measuring CO and/or $CO_2$. A hydrocarbon analyzer will integrate a flame ionization detector. The NOx analyzer operates according to the chemoluminescence technique.

According to another use of the measurement device either additional or alternative, the data acquired by the analysis unit are processed in order to determine the nature and the amount of fumes contained in the sampled exhaust stream. This processing may be carried out with any type of known method and available to one skilled in the art.

In the latter case, it is for example possible to use a filter for acquiring the characteristic data of fumes contained in the sampled exhaust stream. This is the filter which is then utilized for measuring the fume particles present in the exhaust stream over the whole of the sampling surface, or per area according to the number of filters used.

In order to measure the pollutants in the form of fumes, one or several filters will therefore be integrated into the device, so that the exhaust stream crosses this filter. Next, the filter is analyzed with a reflectometer as explained above.

The method proposed above may be applied to the measurement of other types of pollutants other than gases or fumes, like for example fine particles.

All the measurement parameters will be adapted to the needs of the tests, and to the various constraints of hardware, time, and results.

Thus, in order to increase the number of data acquired for processing purposes in order to determine therefrom data on the pollutants, it is for example possible to increase the exploration time of the trajectory, increase the covered trajectory (for example increase the number of circles for a trajectory in circles), increase the acquisition frequency of the data, increase the acquisition rate of the data by the analysis unit.

These parameters should of course be adjusted depending on the constraints, often time constraints, due to the measurements. For example, in the case of measurement of fumes, the mass of filtered gases is today imposed by the ICAO standards (three measurements required between 12 kg and 21 kg of filtered combustion gases at 14 l/min per $m^2$ of filter) and cannot be decreased or increased. Thus, for a given filter, it is possible to select several different filtering times for observing the standard. Only the displacement velocity of the probe is adapted to the resulting filtration times from the standards imposed by the ICAO, and to the radius of the circles covered for a trajectory in circles.

Let us take the particular example of a robot allowing a maximum displacement velocity of the sampling orifice of the probe of 300 mm/s, and with a frequency of the acquisition board of the analysis unit of 10 Hz. According to a trajectory in circles comprising 4 concentric circles, with continuous circular measurements, the most rapid exploration lasts for 16 s, each circle being swept in 4 s, a longer exploration may last for 30 s, 60 s, etc. according to the time limits imposed by the test. The optimum duration of the travel time is determined empirically, by selecting the velocity as large as possible allowing measurements where the concentration peaks of the pollutants are not clipped.

According to the usual dimensions of present aviation engines and the velocity limit of the robot mentioned above, the number of circles used may be comprised between 4 and 8 in order to have a good representation of the pollutants at the outlet of said engine. However, provision may be made for a trajectory in circles having more than 8 circles, if the dimensions of the engine require this or if the accuracy of the measurements carried out of pollutants is desirably increased.

The reader will have understood that many modifications may be brought without materially leaving the novel teachings and the advantages described herein. Therefore, all the modifications of this type are intended to be incorporated inside the scope of the shown measurement method and device.

The invention claimed is:

1. A method for measuring pollutants contained in an exhaust stream at the outlet of an engine, comprising the following steps:
   positioning a probe so that a sampling orifice of said probe is placed on a sampling surface provided at the outlet of the engine in the exhaust stream, and sampling a section of the exhaust stream with said probe;
   activating an analysis unit coupled with the probe in order to carry out acquisition of characteristic data of the exhaust stream sampled by the probe;
   controlling a displacement of the probe in order to impart a continuous displacement of the sampling orifice along a specific trajectory on the sampling surface with constant surface sweeping per unit time, while continuing the sampling and the acquisition of characteristic data of the exhaust stream sampled by the probe, wherein the displacement of the probe is controlled for imparting the continuous displacement of the sampling orifice according to specific trajectories in circles covering the section of the exhaust stream, each circle taking the same amount of time to be swept by the sampling orifice but at different velocities;
   processing the data acquired by the analysis unit in order to measure the pollutants present in the exhaust stream.

2. The method according to claim 1, wherein the specific trajectory in circles is formed with several concentric circles of various radii and of at least one segment connecting each adjacent circle, the circles being covered one after the other inwards or outwards with respect to the center.

3. The method according to claim 1, wherein the specific trajectory in circles is defined by dividing the sampling surface into a plurality of concentric crowns all having an identical area, each circle of the specific trajectory in circles corresponding to a concentric circle positioned in a middle of each crown.

4. The method according to claim 1, wherein a displacement velocity of the sampling orifice of the probe is adapted for each circle of the specific trajectory in circles, so that each circle is covered during the same period.

5. The method according to claim 1, wherein the characteristic data of the exhaust stream sampled by the probe are acquired at the same frequency during the whole measurement.

6. The method according to claim 1, wherein the data acquired by the analysis unit are processed for determining the nature and the concentration of gases contained in the sampled exhaust stream.

7. The method according to claim 1, wherein the data acquired by the analysis unit are processed for determining the nature and the amount of fumes contained in the sampled exhaust stream.

8. The method according to claim 1, wherein a filter is used for acquiring the characteristic data of fumes contained in the sampled exhaust stream, the filter then being studied for measuring the fumes present in the exhaust stream on the whole of the sampling surface.

9. The method according to claim 1, wherein the data acquired by the analysis unit are processed in correlation with the position of the sampling orifice of the probe.

10. The method according to claim 1, comprising a preliminary step for activating the probe in order to begin with sampling gas at the sampling orifice towards the analysis unit.

\* \* \* \* \*